(12) United States Patent
Reaney

(10) Patent No.: US 7,494,662 B2
(45) Date of Patent: Feb. 24, 2009

(54) OIL SOLUBLE PHOTOPROTECTIVE COMPOUNDS AND COMPOSITIONS FROM PLANT OIL PROCESSING

(75) Inventor: Martin J. T. Reaney, Saskatoon (CA)

(73) Assignee: KRU Ltd., Des Moines, IA (US)

( * ) Notice: Subject to any disclaimer, the term of this patent is extended or adjusted under 35 U.S.C. 154(b) by 324 days.

(21) Appl. No.: 10/395,601

(22) Filed: Mar. 24, 2003

(65) Prior Publication Data

US 2003/0186818 A1 Oct. 2, 2003

Related U.S. Application Data

(60) Provisional application No. 60/367,585, filed on Mar. 26, 2002.

(51) Int. Cl.
*A01N 25/00* (2006.01)
*A01N 25/02* (2006.01)
*A01N 25/24* (2006.01)

(52) U.S. Cl. .................................. 424/405; 424/407
(58) Field of Classification Search ............... 424/59; 514/458

See application file for complete search history.

(56) References Cited

U.S. PATENT DOCUMENTS 3,425,938 A * 2/1969 Bloomberg et al. ......... 554/188
4,280,962 A * 7/1981 Watanabe et al. ........... 554/192
5,521,144 A * 5/1996 Farr et al. ................... 504/215

OTHER PUBLICATIONS

Carr, R. A. J. Am. Oil Chemists' Soc. 1976, 53, p. 347-352.*
Mattil, et al. Bailey's Industrial Oil and Fat Products, 3rd edition, John Wiley & Sons: New York, 1964, pp. 719-722, 727-728, 731-733, and 757-760.*

* cited by examiner

*Primary Examiner*—Johann R Richter
*Assistant Examiner*—James H Alstrum Acevedo
(74) *Attorney, Agent, or Firm*—Sturm & Fix LLP

(57) ABSTRACT

Co-product streams derived from the manufacture of vegetable oil were further processed producing materials that possess strong absorbance of visible and ultraviolet light. The compounds contributing to the light absorbance were increased and standardized to produce a fat-soluble composition with consistent and strong absorbance of ultraviolet and visible light. The fat-soluble composition is a useful photoprotective agent for various applications including protection of herbicides and pesticides. In a preferred embodiment acidulated vegetable oil is blended to a constant absorbance of light between 190 and 400 nm and used in a formula to protect a field-applied herbicide.

17 Claims, 1 Drawing Sheet

OIL SOLUBLE PHOTOPROTECTIVE COMPOUNDS AND COMPOSITIONS FROM PLANT OIL PROCESSING

CROSS REFERENCE TO RELATED APPLICATIONS

Figure 1:
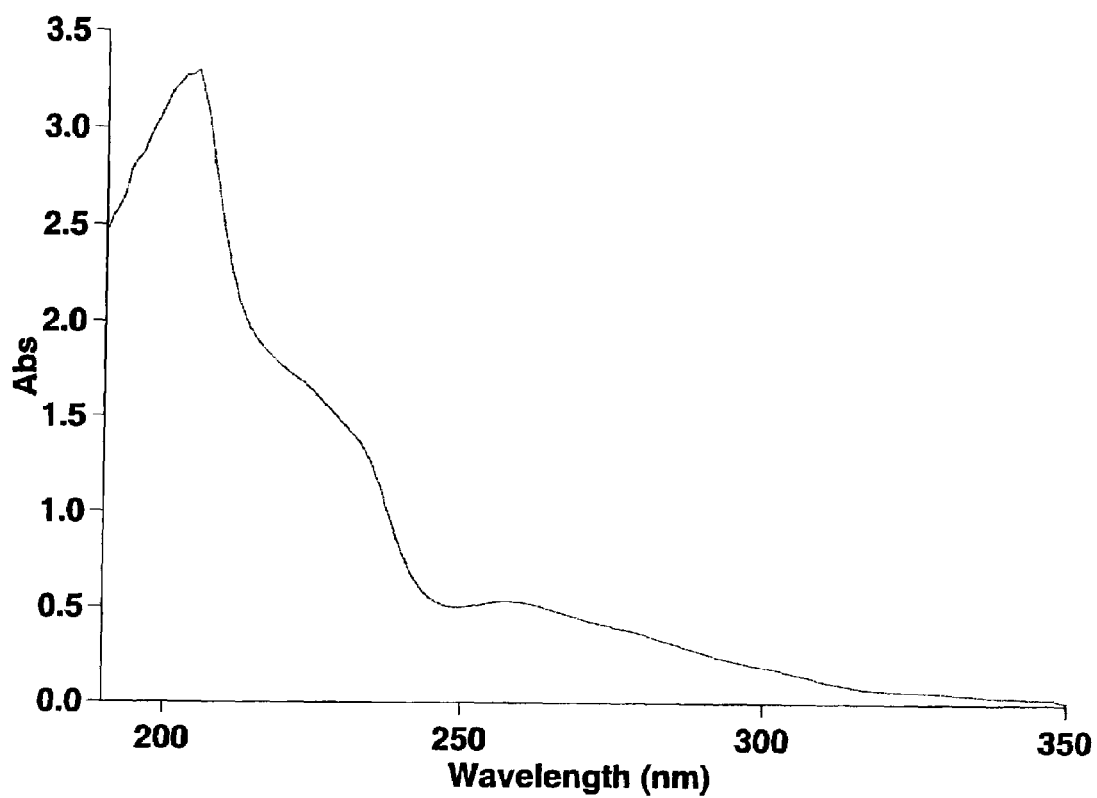

This application contains disclosure from and claims the benefit under Title 35 United States Code § 119(e) of U.S. Provisional Application Ser. No. 60/367,585, filed Mar. 26, 2002 and entitled "Oil Soluble Photoprotective Compounds and Compositions from Plant Oil Processing".

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of photoprotective compounds, and more particularly to photoprotective compounds from plant oil processing.

2. Background Art

Pesticides, herbicides, xenobiotics and other useful chemicals are commonly applied to fields, forests, roadsides and other locations where they may be degraded by exposure to light. Similarly, living organisms including bacteria, bacterial spores, fungi, fungal spores, viruses and viral spores are increasingly being applied in the environment for their beneficial effects. Exposure of these materials and beneficial organisms to light often decreases their effectiveness by altering their chemical structures or diminishing their biological activity. Photoprotective strategies can be employed to maintain or increase the effectiveness of these compounds and organisms.

Wood, plastic, fabric and many other construction materials are also degraded by visible and ultraviolet light. Over time exposure to light will fade or discolour such materials and decrease their integrity. Photoprotective strategies may also be employed to maintain the integrity and appearance of these materials.

Virus particles may be mixed with opaque solids such as carbon black to maintain viability by protection from white light in the method of U.S. Pat. No. 3,541,203. U.S. Pat. No. 5,939,089 teaches methods of coating viral spores with kraft lignin. The coated virus spores possess enhanced resistance to ultraviolet light.

Insecticide compositions containing pyrethinoids are highly susceptible to light degradation. According to U.S. Pat. No. 3,264,176 insecticide powders may be stabilised against light degradation by absorption onto charcoal. The disadvantage of this method is the tendency of dark materials to heat in the environment. Heat as well as light exacerbates the processes involved in degradation and inactivation. Reflective pigments including titanium dioxide can be used in place of carbon black according to U.S. Pat. No. 2,168,064 but the added cost of these materials limits their application. Dextrins and gums also provide protection to pyrethinoids. (U.S. Pat. No. 3,130,121). Strong UV absorbing compounds may be mixed with pyrethinoids to maintain activity. Diisophorone, for example, may be mixed with pyrethinoids to protect them from light wavelengths between 210 and 350 nm according to U.S. Pat. No. 3,839,561. Pyrethinoids may also be stabilized by the addition of amyl-paradimethylamino benzoate and a suitable antioxidant (U.S. Pat. No. 3,560,613).

Endosulfan and chlorpyriphos are also noted to be unstable to light exposure. U.S. Pat. No. 5,549,903 teaches of the use of urea encapsulation and light absorbing compounds to produce a stabilized insecticide product.

Petroleum spray oils may be used to control a number of fungi and insects (U.S. Pat. No. 3,098,000) but these oils are subject to harmful oxidation catalyzed by ultraviolet light. Degradation of the oils causes them to become phytotoxic.

Combinations of anti-oxidants and light absorbents may be added to the oils to prevent degradation and phytoxicity.

Synthetic light absorbing compounds may be highly effective but they are produced from non-renewable resources and they may have undesirable side effects. For example, U.S. Pat. No. 2,772,198 demonstrates that 4-amino-azo-benzene provides excellent protection of pyrethinoids but this compound is a potent carcinogen. Acidulated soybean and other acidulated vegetable oils are commonly used as adjuvants for herbicidal compounds. Gednalske reported that blends of a non-ionic surfactant and acidulated soapstock were effective in preparing a carrier solution for the application of herbicides (U.S. Pat. No. 5,260,260). U.S. Pat. No. 5,521,144 teaches that mixed tocopherols may be added to acidulated soapstock to improve the environmental stability of active ingredients applied with the adjuvant. Acidulated soapstock may also be used in herbicidal compositions to decrease odours as taught by Gednalske and Herzfeld (U.S. Pat. Nos. 5,463,180 and 5,719,102).

Soapstock is a co-product obtained in the manufacture of vegetable oil. It is commonly used in wide-ranging applications including animal feed and road dust control. Industrial soapstock is a highly variable product, which contains significant amounts of pigments, colour bodies and other compounds. Acidulated soapstock is prepared by adding acid to soapstock and recovering oil from the acidified solution. The acidulated oil solution is a concentrated source of plant pigments.

BRIEF SUMMARY OF THE INVENTION

The instant invention discloses the surprising discovery that acidulated soapstock may be prepared to maximize and standardize the content of light absorbing compounds. When appropriately processed the soapstock has sufficient light absorbance to be used as a photoprotective adjuvant for pesticides, herbicides, xenobiotics, other useful chemicals, bacteria, bacterial spores, fungi, fungal spores, viruses and viral spores.

The present invention teaches methods of preparing soapstock to enhance and standardize the light absorbance characteristics. Furthermore, it also teaches the application of acidulated oils as natural photoprotective agents. Acidulated oils with strong light absorbance between 190 and 700 nm wavelength may be used to protect environmentally applied pesticides, herbicides, xenobiotics, other useful chemicals, bacteria, bacterial spores, fungi, fungal spores, viruses and viral spores. Similarly acidulated oils may be able to maintain wood, plastics, fabrics and construction materials that are exposed to visible and ultraviolet light.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a graph illustrating the spectrum of acidulated soapstock diluted to a concentration of 1.0% with n-hexane.

DETAILED DESCRIPTION OF THE INVENTION

The present invention includes methods of preparing acidulated oils with strong light absorbing characteristics. The light absorbance is due to the presence of specific compounds that may be preferentially concentrated during soapstock preparation or during acidulation. The light absorbing oil soluble compounds include but are not limited to naturally occurring oil soluble protein, tocopherol, phaeophytin, carotenoid, quinone, quinol, phenolic, and ferulate ester. The light absorbing oil also includes chemically modified compounds where the modification is controlled by extraction and acidulation conditions.

The invention also teaches that although all acidulated soapstock has some light absorbance the absorbance characteristics are too variable for the reliable production of a useful light adsorbing oil. The light adsorbing quality of the oil is subject to wide ranging factors. Compounds present in the acidulated oil vary considerably depending on the species and genetic factors. The utilisation of soapstock from the processing of soy, canola, rapeseed, palm, sunflower, peanut, cottonseed, flax, rice bran is included in the current invention. In a preferred embodiment acidulated soapstock derived from the manufacture of soybean oil is utilized for its photoprotective effects. In another preferred embodiment acidulated soapstock are blended to minimise differences in light absorbance and to produce a consistent product.

Furthermore, conditions used in oil extraction by different commercial operations greatly affect the light absorbance properties of the soapstock. For example, in one industrial process soapstock is prepared such that it includes phospholipids and glycolipids as a major component while other soapstock has only minor amounts of these compounds. Phospholipids significantly affect the light absorbance of the acidulated oil. The current invention includes but is not restricted to acidulated oils that are produced from soapstock materials that include phospholipids and glycolipids.

Oil extrusion, tempering conditions, expeller pressing and solvent extraction methods vary between manufacturers of vegetable oil. These processing methods alter the light absorbance characteristics of the soapstock. It is also part of the current invention to utilize extraction protocols such as modified extrusion methods, expeller pressing and solvent extraction to enhance the light absorbance of the acidulated oil. In a preferred embodiment of the current invention the soapstock is derived from expeller pressed oils. In another embodiment the soapstock is derived from solvent extracted oils. The soapstock may also be recovered from mixtures of solvent extracted oils and expeller pressed oils.

Conditions employed during acidulation also affect the absorbance of the oil. For example, the temperature of acidulation, the type of acid used for acidulation and duration of the acidulation treatment significantly affect oil light absorbance properties. The current invention includes conditions that occur during acidulation that enhance or alter oil absorbance properties. In a preferred embodiment the acidulation occurs at a pH of less than 2.0. In another preferred embodiment the acidulation occurs at a pH of 1.5 and a temperature of 90-110 C. In another preferred embodiment sulfuric acid is used to acidulate the oil. It is known to those skilled in the art that any of a number of mineral and organic acids may be used for acidulation. Due to the price of the acid used it may be preferred to utilize sulfuric acid.

Normally the major components of acidulated oils are fatty acids, partial glycerides and triglycerides. The fatty acids and glycerides themselves have only limited light absorbance characteristics, with a strong absorbance due to their carbonyl functionality at wavelengths less than 210 nm. Therefore, the glycerides act to dilute the light absorbing compounds. Selectively removing fatty acids and glycerides can concentrate the light absorbance of the oil producing intensely absorptive oil. In particular, it is possible to selectively remove fatty and mono glycerides from acidulated oils by distillation. It is an embodiment of this invention where fatty acids and glycerides are removed from acid oil to increase the concentration of light absorbance. In a preferred embodiment fatty acids are removed from the acid oil by distillation. In another preferred embodiment fatty acids are removed from the acid oil by short path distillation.

The light absorbance characteristics of acidulated oils are not equal at all wavelengths. It is possible to augment the light absorbance characteristics by the addition of oil soluble pigments. Pigments from naturally occurring sources are preferred but the use of synthetic pigments is an embodiment of the current invention.

The photoprotective acidulated fatty acids may be used in any application for protection of light exposed materials. In a preferred embodiment the photoprotective action is utilised in herbicide spray mixtures to maintain the biological activity of the herbicide. In another preferred embodiment the photoprotective action is used to stabilise wood against chemical attack.

EXAMPLES

Example 1

Laboratory Preparation of Acidulated Canola Oil and its Light Absorbance Characteristics Canola soapstock was obtained from a commercial manufacturer of vegetable oil. Four hundred grams of the soapstock were blended with 24 grams of sulfuric acid in a 4-liter glass beaker using a stainless steel spatula. The mixture was heated 95 C then held at that temperature for 15 minutes on a hot plate equipped with a teflon coated magnetic stirrer bar. After acidulation the contents of the beaker were cooled. The beaker contents were transferred to a separatory funnel where, after settling, the lower water layer was removed (221 g—water). An intermediate layer of viscous material was then taken from the funnel (12 g—emulsion) followed by an upper layer of black coloured oil (181 g—of acidulated soapstock). The extracted oil was dissolved to a concentration of 10%, 1.0%, 0.1% and 0.01 w/w in spectrophotometry grade n-hexane.

Visible and ultraviolet light spectra of all dilutions of acidulated soapstock were measured using a dual beam UV/visible spectrophotometer. The spectrum of the 1.0% dilution is shown in FIG. 1.

Example 2

Commercial Scale Acidulation of Soy Oil

Soybean soapstock was obtained from a commercial manufacturer of vegetable oil. Four thousand pounds of sulfuric acid was added to eighty thousand pounds of soapstock with continuous agitation in a fiberglass resin reactor tank. The temperature of the mixture was increased to 95 C by injection of steam while maintaining continuous agitation. After addition of acid and heat treatment the mixture was subject to 2 additional hours of agitation at 95 C the contents of the reactor tank were transferred to a settling tank. After 24 hours 35,000 pounds of acidulated oil were removed from the top of the tank. The oil possessed strong UV absorbance characteristics.

Example 3

Greenhouse Performance of Grass Herbicides as Influenced by Adjuvants Including Using an Acidulated Oil as an Adjuvant Spray mixtures of the herbicides (+/−) 2-{(E)-1-{3-chloroallyloxyimino]propyl]-5-{2-(ethylthio)propyl}-hydroxycyclohexen-2-one (Select) and 2-{1-(ethoxyimino)butyl}-5-[2-(ethylthio)propyl]-3-hydroxy-2-cyclohexen-1-one (Poast) were prepared with an non-ionic surfactant adjuvant including acidulated soybean oil and without the acidulated oil. The non-ionic surfactants were added to a water spray solution at a concentration of 0.25% v/v ai and applied to yellow foxtail plants in the greenhouse. The application rate of Select and Poast was 2 fl. and 6 fl. Oz/Acre, respectively. Control of grassy weeds was assessed as reduction in dry weight of the plants compared to untreated control plants 27 days after application. Control data was statistically analyzed using analysis of variance methods. Differences between means reported in the Table I were determined at p=0.05 using the Student-Newman-Keuls method.

Field Performance of a Grass Control Herbicide as Influenced by Adjuvants Including Using Acidulated Oil as an Adjuvant.

Spray mixtures of the herbicide (+/−) 2-{(E)-1-{3-chloroallyloxyimino]propyl]-5-{2-(ethylthio)propyl}-hydroxycyclohexen-2-one (Select) was prepared with a non-ionic surfactant adjuvant including acidulated soybean oil and without the acidulated oil. The nonionic surfactants were used at a concentration of 0.25% v/v ai and applied to corn and wheat plants in the field. The application rate was 2 fl. oz./Acre. Percent control of the corn and hard red spring wheat was visually assessed compared to untreated control plants 17 and 31 days after treatment. Control data was statistically analyzed using analysis of variance methods. Differences between means reported in the Table II were determined at p=0.05 using the Student-Newman-Keuls method.

Table II shows that when Select was applied without an adjuvant weed control was poor. Inclusion of an adjuvant improved control of the corn while inclusion of a non-ionic surfactant with the acidulated oil increased control even more.

TABLE II

| Treatment | Corn Percent control* 17 days after application | Corn Percent control* 31 days after application | Wheat Percent control* 17 days after application | Wheat Percent control* 31 days after application |
|---|---|---|---|---|
| Select (no adjuvant) | 10 c** | 19 d | 15 d | 30 g |
| Select (NIS) | 123 c | 40 c | 34 d | 75 e |
| Select (NIS + acid. oil w/o strong UV absorbance) | 19 c | 47.5 c | 31 d | 80 de |
| Select (NIS + acid. oil w strong UV absorbance) | 58 b | 68 b | 59 c | 85 cd |

*Percent control assessed visually compared to untreated controls.
**Means followed by the same letter do not significantly differ (P = 0.05 Student-Neuman-Keuls)

TABLE I

| Treatment | Barnyard grass Percent control* 27 days after application | Yellow Foxtail Percent control* 27 days after application | Field Sandbur Percent control* 27 days after application |
|---|---|---|---|
| Select (no adjuvant) | 62 h | 62 e | 48 c |
| Select (NIS) | 94 b | 72 d | 67 b |
| Select (NIS + acid. oil w/o strong UV absorbance) | 100 a | 75 cd | 75 a |
| Select (NIS + acid. oil w strong UV absorbance) | 100 a | 78 bc | 77 a |
| Poast (no adjuvant) | 62 h | 52 f | 38 ef |
| Poast (NIS) | 86 d | 72 d | 67 b |
| Poast (NIS + acid. oil w/o strong UV absorbance) | 90 c | 82 b | 72 a |
| Poast (NIS + acid. oil w strong UV absorbance) | 96 b | 87 a | 73 a |

*Percent reduction in dry weight compared to untreated control plants.
** Means followed by the same letter do not significantly differ (P = 0.05 Student-Neuman-Keuls)

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

I claim:

1. A method of producing a pesticide adjuvant, comprising the steps of: adding acid to a vegetable soapstock until a pH of about 2.0 is attained; maintaining temperature of acidulated vegetable soapstock in a range of about 90-110° C. during acidulation for a predetermined processing time; and removing fatty acids, monoglycerides, and glycerides from the acidulated vegetable soapstock to concentrate the light absorbance of the acidulated vegetable soapstock, wherein a 1 mm layer of the acidulated vegetable soapstock absorbs greater than 99% of impingent UV-A and UV-B radiation.

2. The method of claim 1 wherein the vegetable soapstock is selected from a group consisting of soybean, sunflower, palm, safflower, rice bran, rapeseed, flaxseed and olive oils.

3. The method of claim 1 wherein the acid is a mineral acid.

4. The method of claim 3 wherein the mineral acid is selected from a group consisting of sulphuric acid, hydrochloric acid, nitric acid and phosphoric acid.

5. The method of claim 1 wherein the acid is an organic acid.

6. The method of claim 5 wherein the organic acid is selected from a group consisting of citric acid, acetic acid, lactic acid, propionic acid, tartaric acid and carbonic acid.

7. The method of claim 1 wherein the pH is in the range of about 2.0 to 1.0.

8. The method of claim 1 wherein the temperature is maintained at about 95° C.

9. The method of claim 1 wherein the predetermined processing time is about 2.0 hours.

10. The method of claim 1 wherein the compounds are removed by distillation.

11. The method of claim 1 further including the step of diluting the acidulated vegetable soapstock to achieve a material that absorbs greater than 99.5% of impingent UV-A and UV-B radiation.

12. The method of claim 11 wherein the acidulated vegetable soapstock is diluted with n-hexane.

13. A method of protecting a material from light degradation by applying the acidulated vegetable soapstock produced by the method of claim 1.

14. The method of claim 13 wherein the material protected is selected from a group consisting of pesticides, herbicides, xenobiotics, bacteria, bacterial spores, fungi, fungal spores, viruses, viral spores, wood, plastics and fibers.

15. The method of claim 14 wherein the acidulated vegetable soapstock has a constant absorbance of light between 190 and 400 nm, and wherein it is applied to a field-applied herbicide.

16. The method of claim 15 wherein a 1 mm layer absorbs greater than 99% of impingent UV-A radiation.

17. The method of claim 15 wherein a 1 mm layer absorbs greater than 99% of impingent UV-B radiation.

* * * * *